United States Patent [19]

Hess et al.

[11] Patent Number: 4,778,911
[45] Date of Patent: Oct. 18, 1988

[54] PROCESS FOR PREPARATION OF 3-(ACYL)AMINO-4-ALKOXY-PHENYL-β-HYDROXYETHYL-SULFONE (SULFONATES)

[75] Inventors: Peter Hess, Hofheim am Taunus; Folker Kohlhaas, Hochheim am Main; Theodor Papenfuhs, Frankfurt am Main, all of Fed. Rep. of Germany

[73] Assignee: Hoechst Aktiengesellschaft, Frankfurt am Main, Fed. Rep. of Germany

[21] Appl. No.: 65,678

[22] Filed: Jun. 18, 1987

Related U.S. Application Data

[63] Continuation of Ser. No. 772,632, Sep. 5, 1985, abandoned.

[30] Foreign Application Priority Data

Sep. 7, 1984 [DE] Fed. Rep. of Germany ....... 3432891

[51] Int. Cl.$^4$ ............... C07C 141/16; C07C 103/127; C07C 103/22
[52] U.S. Cl. ...................... 558/33; 564/49; 564/184; 564/218; 564/223
[58] Field of Search ................ 260/543 R, 513.7; 564/184, 218, 49, 223; 558/33, 26

[56] References Cited

FOREIGN PATENT DOCUMENTS 573193 3/1933 Fed. Rep. of Germany .
6722767 11/1967 Japan .

OTHER PUBLICATIONS

J. Chem. Soc., 1926, p. 2699.

Primary Examiner—Nicky Chan

[57] ABSTRACT

A process for the preparation of 3-(acyl)amino-4-alkoxy-phenyl-β-hydroxyethyl-sulfone (sulfates) of the formula (1)

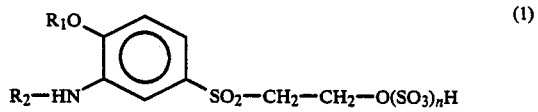

in which $R_1$ is alkyl having 1–4 carbon atoms and $R_2$ is hydrogen or one of the groupings

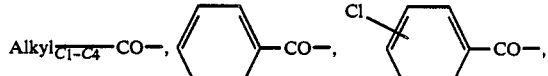

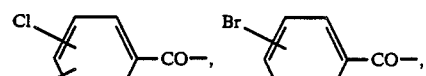

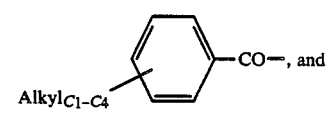

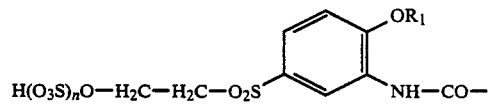

with the proviso that $n=1$ if $R_2=H$ and $n=0$ if $R_2=$ acyl, by converting 2-alkoxyacylanilines of the formula (2)

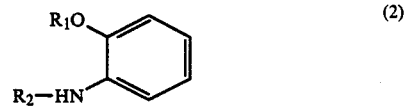

in which $R_1$ and $R_2$ have the meanings given, in a known manner to the corresponding sulfochlorides substituted in the p-position relative to the alkoxy group, reducing the sulfochlorides with an alkali metal sulfite or ammonium sulfite in an aqueous medium at pH 7.0–8.5 and at $-5$ to $+40°$ C. to give the corresponding sulfinates, alkoxylating the latter with ethylene oxide in an aqueous medium at pH 6.0–8.5 and 40°–80° C. to give the 3-acylamino-4-alkoxyphenyl-β-hydroxyethyl-sulfones of the formula (1) (with $R_2=$acyl and $n=0$) and, if appropriate, esterifying the latter, with deacylation, with concentrated sulfuric acid at 70°–150° C. to give the compounds of the said formula (1) (with $R_2$H and $n=1$).

5 Claims, No Drawings

PROCESS FOR PREPARATION OF 3-(ACYL)AMINO-4-ALKOXY-PHENYL-β-HYDROXYETHYL-SULFONE (SULFONATES)

This case is a continuation of our copending application Ser. No. 772,632, filed Sept. 5, 1985, now abandoned.

The present invention relates to a novel process, substantially improved over the known process, for the preparation of 3-(acyl)amino-4-alkoxyphenyl-β-hydroxyethyl-sulfone (sulfates) of the general formula (1) given below, in a high yield and with excellent quality, and also with a considerably reduced acid load and organic load in the mother liquors, in a technically simple manner which is acceptable under safety engineering aspects.

The compounds of the general formula (1) (with $R_2=H$ and $n=1$), given below, represent important industrial intermediates for the production of fiber-reactive dyes, such as are described, for example, in German Offenlegungsschrift No. 3,009,522 (U.S. Pat. No. 4,407,748).

The preparation has hitherto been carried out by a technically involved process, which requires improvements under safety aspects, by chlorosulfonation of o-nitro-alkoxybenzenes, reduction of the 2-nitro-alkoxybenzene-4-sulfochlorides by means of sulfite, conversion of the resulting 2-nitro-alkoxybenzene-4-sulfinates with ethylene oxide to give the 2-nitro-alkoxyphenyl-4-β-hydroxyethyl-sulfones and reduction of the latter to the 2-amino-alkoxyphenyl-4-β-hydroxyethyl-sulfones (cf. Japanese Application No. 67/22,767). Finally, the aliphatic hydroxyl group is esterified (conversion of the β-hydroxyethyl-sulfones into the corresponding sulfuric acid half esters) (cf. German Pat. No. 1,443,877 (U.S. Pat. No. 3,414,579)).

This process is technically unsatisfactory in several respects:

1. The chlorosulfonation of 2-nitro-alkoxybenzenes is carried out with chlorosulfonic acid in the presence of sodium chloride at temperatures which are close to the decomposition point of the reaction mixture. This requires a large outlay on controls, to ensure exact temperature control (expensive apparatus).
2. For safety reasons, the chlorosulfonation must be carried out in high dilution, i.e. with large quantities of chlorosulfonic acid, and this results in high acid and salt loads in the mother liquors, causing disposal problems.
3. The yields in the chlorosulfonation, reduction and ethoxylation are only moderate, the quality of the end products is unsatisfactory, in part also for this reason, and the high organic load in the effluents arises, which make biological treatment very expensive.

There was therefore an urgent need to make the industrially valuable intermediates of the general formula (1), given below, available by routes which show these disadvantages only to a minor degree or not at all and thus make their production less polluting and more economical.

The stated object is achieved in an extremely advantageous manner by the process according to the invention.

It has been found that the 3-(acyl)amino-4-alkoxyphenyl-β-hydroxyethyl-sulfone (sulfates) of the general formula (1)

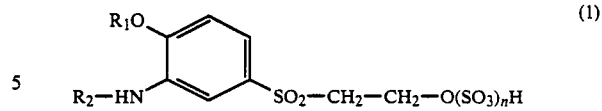

in which $R_1$ is an alkyl group having 1–4 carbon atoms, for example a methyl, ethyl, propyl or butyl group, and $R_2$ is a hydrogen atom or a grouping from the series

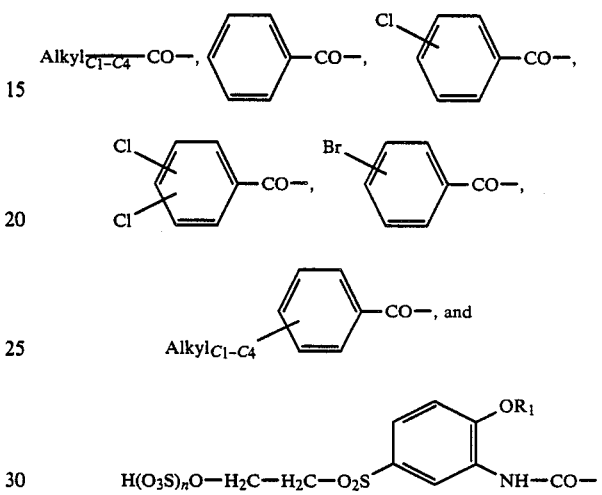

with the proviso that $n=1$ if $R_2=H$ and $n=0$ if $R_2=$acyl, can be produced in a high yield and in excellent quality by converting alkoxyacylanilines of the general formula (2)

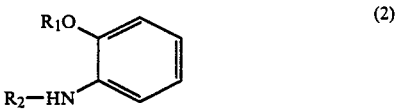

in which $R_1$ and $R_2$ have the meanings given above, with chlorosulfonic acid in a known manner (German Pat. No. 573,193 (Frdl. 19, 699–701)) to give the corresponding sulfochlorides substituted in the 4-position relative to the alkoxy group, reducing the sulfochlorides with alkali metal sulfite or ammonium sulfite in an aqueous medium at a pH value of 7.0–8.5, preferably 7.5–8.0, at a temperature of −5° to +40° C., preferably 0°–20° C., to give the corresponding sulfinates, ethoxylating the latter with ethylene oxide in an aqueous medium at a pH value of 6.0–8.5, preferably 7.0–7.5, and at a temperature of 40°–80° C., preferably 55°–65° C., to give the 3-acylamino-4-alkoxyphenyl-β-hydroxyethylsulfones of the said formula (1) (with $R_2=$acyl and $n=0$) and, if appropriate, esterifying the latter, with deacylation, with concentrated sulfuric acid at temperatures of 70°–150° C., preferably 85°–135° C., to give the compounds of the said general formula (1) (with $R_2=H$ and $n=1$).

This is to be regarded as extremely surprising, inasmuch as m-substituted benzene-sulfochlorides on reduction with sulfite give only moderate yields (maximum 60–70%) of the corresponding sulfinates. This fact (see above) known for 3-nitrobenzenesulfochlorides and 3-nitro-4-alkoxy-benzene-sulfochlorides was confirmed by our own investigations also for 3-acylaminobenzenesulfochlorides, since these can be reduced with sulfite only to a maximum extent of 55% to the 3-acylamino-benzene-sulfinates.

It was therefore not to be expected that, in contrast to the abovementioned sulfochlorides, 3-acylamino-4-alkoxybenzene-sulfochlorides can be converted with sulfite almost quantitatively, i.e. in yields above 95%, into the desired 3-acylamino-4-alkoxybenzene-sulfinates.

The acid deacylation of the compounds of the general formula (1) (with $R_2$=acyl and n=0) and the esterification of the 2-amino-alkoxybenzene-4-$\beta$-hydroxyethyl-sulfones thus obtained with concentrated sulfuric acid to give the target compounds of the formula (1) (with $R_2$=H and n=1) are admittedly known as individual reactions, but they are combined in one reaction step in the process according to the invention and are thus rendered particularly economical.

In detail, the process is carried out in such a way that the 2-acylamino-alkoxybenzene-4-sulfochloride, freshly prepared according to German Pat. No. 573,193 and moist with water, or subsequently isolated in the dry state from a suitable solvent and hence storage-stable, is introduced at a pH value of 7.0–8.5, preferably 7.5–8.0, within 0.5–2 hours into aqueous alkali metal sulfite solution at −5° to +40° C., preferably 0° to 20° C., the pH being held within the said range by metering in an alkali metal hydroxide solution, preferably sodium or potassium hydroxide solution.

The sulfite is used in an at least stoichiometric quantity. It is advantageous to employ the sulfite in an excess of 5–30 mol percent.

The resulting solution of the 2-acylamino-alkoxybenzene-4-sulfinates is treated directly with ethylene oxide (1.5–4.5 mol, preferably 2.0–3.5 mol per mol of sulfinate) at a pH value of 6.0–8.5, preferably 7.0–7.5, and at a temperature of 40°–80° C., preferably 55°–65° C., within 6–8 hours, the pH being held within the optimum range by means of metering in an aqueous mineral acid, preferably sulfuric acid or phosphoric acid. The ethylene oxide is employed in an at least stoichiometric quantity.

After the end of the reaction and cooling to room temperature, the 2-acylamino-alkoxybenzene-4-$\beta$-hydroxyethyl-sulfone, precipitating in a crystalline form during the reaction, is isolated in high yield by filtration.

The esterification with deacylation is advantageously carried out in such a way that a mixture of stoichiometric quantities of 2-acylamino-alkoxybenzene-4-$\beta$-hydroxyethyl-sulfone and concentrated sulfuric acid (i.e. in a molar ratio of 1:1 to 1:1.2) is heated in an industrially conventional mixer unit (for example a drying pan, kneader or paddle drier), preferably in vacuo, to temperatures of 70° to 150° C., preferably 85° to 135° C., and the vapors formed (water and the carboxylic acid or $CO_2$ eliminated) is discharged from the reactor. The conversion is complete when vapors are no longer observed. The sulfuric acid half ester of the 2-amino-alkoxyphenyl-hydroxyethyl-sulfone (formula (1) with $R_2$=H and n=1) formed in a quantitative reaction is present in the reactor as a dry, freeflowing powder which can be employed directly for subsequent reactions. (If, depending on the hydroxyethyl-sulfone to be converted, a certain excess of concentrated sulfuric acid is advisable, this should not exceed a 5-molar excess).

The process according to the invention enables the target compounds of the said formula (1) to be prepared particularly economically by a novel route, which proceeds in all stages at very high yields, an excellent quality and with a considerably reduced acid load and organic load in the mother liquors, as compared with the state of the art, in a manner which is industrially simple and acceptable under safety engineering aspects, and thus represents a considerable technical advance.

The examples which follow are intended to explain the process in more detail, without restricting it thereto.

EXAMPLE 1

265 parts of 2-acetaminoanisole-4-sulfochloride (for example prepared according to German Pat. No. 573,193, Example 1) are added in portions within 30–45 minutes to a stirred mixture of 303 parts of 40% aqueous sodium hydrogen sulfite solution, 143 parts of 33% aqueous sodium hydroxide solution, 9 parts of 85% aqueous phosphoric acid and 1,000 parts of water at 0° C., which mixture has a pH of 7.5. During the addition, the temperature is held below 20° C. by external cooling and the pH value is held at 7.5–8.0 by dropwise addition of a total of 246 parts of 33% aqueous sodium hydroxide solution. The temperature is then allowed to rise to 25°–30° C., everything going in the solution within the period of about 1 hour.

139 parts of liquid ethylene oxide are then injected, with stirring, from a cooled receiver into the sulfinate solution below the surface and the mixture is then heated to 60° C. In order to avoid an escape of ethylene oxide from the reaction vessel, the latter carries a brine-cooled double-surface condenser.

Stirring is continued for 6–7 hours at 60°–70° C., the pH value being kept constant by dropwise addition of a total of 532 parts of 20% aqueous sulfuric acid.

After cooling to room temperature, the 2-acetamino-anisole-4-$\beta$-hydroxyethyl-sulfone which has precipitated is filtered off such suction and dried at 100° C. in a circulating-air oven. This gives 297 parts of a salt-containing product with a purity of 92.5% determined by HPLC (=high performance liquid chromatography), which corresponds to a yield of 99% of theory, relative to 2-acetamino-anisole-4-sulfochloride.

EXAMPLES 2–6

Using aliquot parts of the 2-acylamino-alkoxybenzene-sulfochlorides of the formula (3), listed in the Table below and prepared, for example, by the process of German Pat. No. 573,193, and in other respects following the procedure indicated in Example 1, the corresponding 2-acylamino-alkoxybenzene-4-$\beta$-hydroxyethyl-sulfones of the formula (4) are obtained in the yields and purities indicated in Table I.

TABLE I

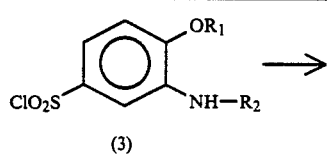

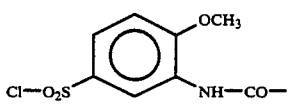

| Example | $R_1$ | $R_2$ | Yield | Purity |
|---------|-------|-------|-------|--------|
| 2 | $C_2H_5$ | $CO-CH_3$ | 97.5% | 92.8% |
| 3 | $CH_3$ | A* | 99.1% | 96.5% |
| 4 | $CH_3$ | $CO-C_6H_5$ | 98.9% | 95.8% |
| 5 | $C_4H_9$ | $CO-CH_3$ | 96.2% | 90.5% |
| 6 | $CH_3$ | $CO-C_2H_5$ | 98.0% | 92.4% |

*A denotes the radical of the formula

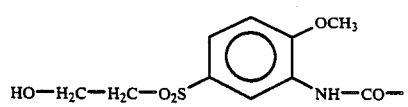

EXAMPLE 7

1,200 parts of 91% pure 2-acetamino-anisole-4-β-hydroxyethyl-sulfone (prepared according to Example 1) are introduced into a kneader. 442 parts of 96% sulfuric acid are allowed to run in within 15 minutes, with the kneading tools (Sigma blades) running. The jacket of the pan is heated with steam to 95°–100° C., and a reduced pressure of 150–200 mm Hg is applied to the tight-sealing pan cover, in which a vacuum connection is provided. Under these conditions, the deacetylation and, in parallel thereto, the esterification proceed quantitatively within 6–8 hours. Because of the reduced pressure, the resulting vapors (water and acetic acid) have completely distilled out of the reaction mixture and can be condensed out virtually quantitatively in a cooled distillate receiver fitted between the vacuum generator and the kneading pan.

After the reaction, the pan jacket is cooled with water, while the kneading tools are running, and the reaction product is isolated as an almost colorless powder from the kneader. This gives 1,290 parts of 2-amino-anisole-4-β-sulfatoethyl-sulfone of a purity of 95.0% (by diazotization) which corresponds to a yield of 98.6% of theory.

If, in place of the kneader, another industrially usual mixing or drying unit, for example a drying pan or a paddle drier, is used and the procedure followed is as indicated in other respects, the product is obtained in a comparable yield and quality.

EXAMPLES 8–12

If, in place of 2-acetamino-anisole-4-β-hydroxyethyl sulfone, aliquot parts of the compounds of the formula (4), as listed in the Table below, are employed and in other respects the procedure of Example 7 is followed, the target compounds of the formula (5) are obtained in likewise almost quantitative yield with the purity indicated in each case in Table II and determined by diazotization.

TABLE II

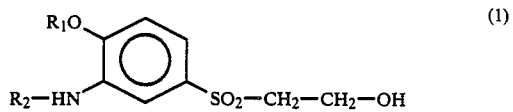

| Example | $R_1$ | $R_2$ | Purity |
|---------|-------|-------|--------|
| 8 | $CH_3$ | A | 97.2% |
| 9 | $CH_3$ | $-CO-C_2H_5$ | 96.0% |
| 10 | $CH_3$ | $-CO-C_3H_7$ | 94.2% |
| 11 | $C_2H_5$ | $-CO-CH_3$ | 95.8% |
| 12 | $C_4H_9$ | $-CO-CH_3$ | 93.8% |

*A denotes the radical of the formula

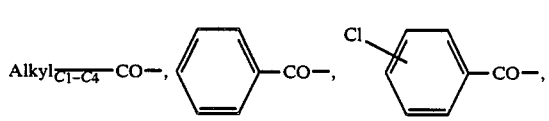

What is claimed is:

1. A process for the preparation of 3-substituted-4-alkoxyphenyl-β-hydroxyethyl-sulfones of the formula (1)

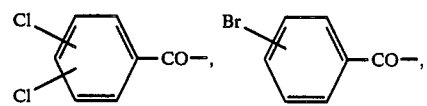

in which $R_1$ is an alkyl group having 1–4 carbon atoms and $R_2$ is an acyl or amido group of the formula

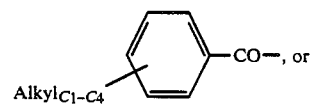

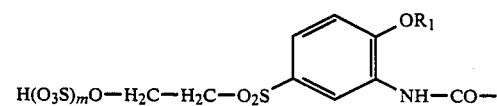

and m is zero or 1, which comprises converting 2-alkoxyacylanilines of the formula (2)

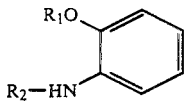
(2)

in which $R_1$ and $R_2$ are as defined previously, to the corresponding sulfochlorides substituted in the p-position relative to the alkoxy group, reducing the sulfochlorides with alkali metal sulfite or ammonium sulfite in an aqueous medium at a pH value of 7.0–8.5 and at a temperature of −5° to +40° C. to give the corresponding sulfinates, alkoxylating the latter with ethylene oxide in an aqueous medium at a pH value of 6.0–8.5 and at a temperature of 40°–80° C. to give a 3-($R_2$NH)-substituted-alkoxyphenyl-β-hydroxyethyl-sulfone compound of the said formula (1).

2. A process as claimed in claim 1 wherein $R_2$ is a said acyl group.

3. A process as claimed in claim 1 wherein m is zero.

4. A process as claimed in claim 1 wherein $R_2$ is said amido group.

5. A process for the preparation of 3-amino-4-alkoxyphenyl-β-hydroxyethyl-sulfone sulfates of the formula (1')

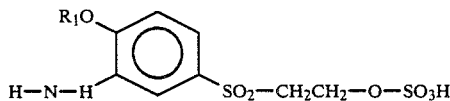
(1')

in which $R_1$ is an alkyl group having 1 to 4 carbon atoms, which comprises converting 2-alkoxyacylanilines of the formula (2)

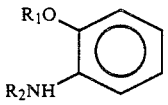
(2)

in which $R_1$ is as defined previously and $R_2$ is an acyl or amido group of the formula

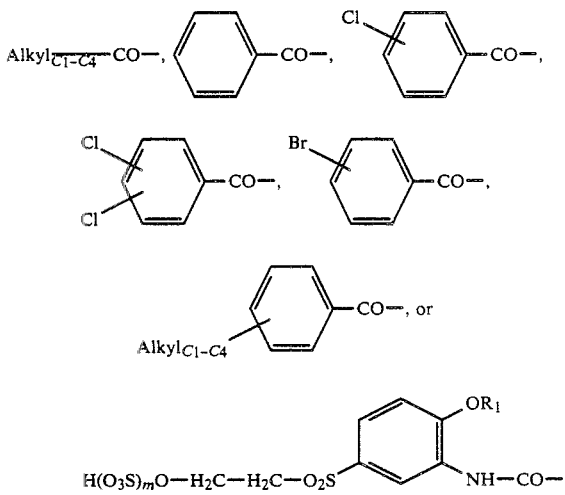

wherein $R_1$ is as defined previously and m is zero or 1, to the corresponding sulfo-chlorides substituted in the p-position relative to the alkoxy group, reducing the sulfochlorides with alkali metal sulfite or ammonium sulfite in an aqueous medium at a pH value of 7.0–8.5 and at a temperature of −5° to +40° C. to give the corresponding sulfinates, alkoxylating the latter with ethylene oxide in an aqueous medium at a pH value of 6.0–8.5 and at a temperature of 40°–80° C. to give the 3-($R_2$—NH)-substituted-4-alkoxyphenyl-β-hydroxyethyl-sulfone compound, said esterifying and deacylating said 3-($R_2$—NH)-substituted-4-alkoxyphenyl-β-hydroxyethyl-sulfone compound with concentrated sulfuric acid at a temperature of 70°–150° C. to provide a sulfate of said formula (1').

* * * * *

UNITED STATES PATENT AND TRADEMARK OFFICE
CERTIFICATE OF CORRECTION

PATENT NO. : 4,778,911
DATED : October 18, 1988
INVENTOR(S) : Peter Hess, Folker Kohlhaas, Theodor Papenfuhs It is certified that error appears in the above-identified patent and that said Letters Patent is hereby corrected as shown below:

In claim 5, line 42 of column 8, "said" should read --and-- before "esterifying".

Signed and Sealed this

Eighth Day of August, 1989

Attest:

DONALD J. QUIGG

Attesting Officer

Commissioner of Patents and Trademarks